United States Patent
Xu et al.

(10) Patent No.: US 10,632,100 B2
(45) Date of Patent: Apr. 28, 2020

(54) APPLICATION OF OBACUNONE IN PREPARATION OF DRUG FOR PREVENTING AND TREATING LUNG DAMAGE AND PULMONARY FIBROSIS

(71) Applicant: GUANGDONG PROVINCIAL HOSPITAL OF TRADITIONAL CHINESE MEDICINE, Guangzhou, Guangdong Province (CN)

(72) Inventors: Yang Xu, Guangzhou (CN); Shengmei Xu, Guangzhou (CN); Weimin Chen, Guangzhou (CN)

(73) Assignee: GUANGDONG PROVINCIAL HOSPITAL OF TRADITIONAL CHINESE MEDICINE, Guangzhou, Guangdong (CN)

( * ) Notice: Subject to any disclaimer, the term of this patent is extended or adjusted under 35 U.S.C. 154(b) by 0 days.

(21) Appl. No.: 16/068,014

(22) PCT Filed: Feb. 28, 2017

(86) PCT No.: PCT/CN2017/075179
§ 371 (c)(1),
(2) Date: Jul. 3, 2018

(87) PCT Pub. No.: WO2017/152796
PCT Pub. Date: Sep. 14, 2017

(65) Prior Publication Data
US 2019/0046502 A1 Feb. 14, 2019

(30) Foreign Application Priority Data
Mar. 9, 2016 (CN) .......................... 2016 1 0133807

(51) Int. Cl.
| | | |
|---|---|---|
| A61K 31/366 | (2006.01) |
| A61P 11/00 | (2006.01) |
| A61K 9/00 | (2006.01) |
| A61K 9/20 | (2006.01) |
| A61K 9/48 | (2006.01) |
| A61K 47/10 | (2017.01) |
| A61K 47/12 | (2006.01) |
| A61K 47/24 | (2006.01) |
| A61K 47/44 | (2017.01) |

(52) U.S. Cl.
CPC .......... *A61K 31/366* (2013.01); *A61K 9/0019* (2013.01); *A61K 9/2013* (2013.01); *A61K 9/2054* (2013.01); *A61K 9/4858* (2013.01); *A61K 9/4866* (2013.01); *A61K 47/10* (2013.01); *A61K 47/12* (2013.01); *A61K 47/24* (2013.01); *A61K 47/44* (2013.01); *A61P 11/00* (2018.01)

(58) Field of Classification Search
USPC ........................................................ 514/450
See application file for complete search history.

(56) References Cited

FOREIGN PATENT DOCUMENTS

| | | |
|---|---|---|
| CN | 105147703 A | 12/2015 |
| CN | 105769880 A | 7/2016 |
| WO | 02072120 A1 | 9/2002 |

OTHER PUBLICATIONS

Gong, Wei et al., "Simultaneous Determination of Dictamnine, Obacunone and Fraxinellone in Dictamni cortex Dispensing Granules by HPLC", Modernization of Tradition Al Chinese Medicine and Materia Medica—World Science and Technology, Traditional Chinese Medicine Research, vol. 17, No. 1, Dec. 31, 2015 (Dec. 31, 2015), pp. 129-132.

Han, Xueqing et al., "Research progress in biological activity and structure-activity relationship of Limonoids", Progress in Pharmaceutical Sciences, vol. 39, No. 10, Dec. 31, 2015 (Dec. 31, 2015), pp. 775-780.

International Search Report & Written Opinion dated May 26, 2017 from PCT Application No. PCT/CN2017/075179.

Xu, Shengmei et al., "Obacunone activates the Nrf2-dependent antioxidant responses", Protein Cell, vol. 7, No. 9, Aug. 16, 2016 (Aug. 16, 2016), pp. 684-688.

*Primary Examiner* — Marcos L Sznaidman
(74) *Attorney, Agent, or Firm* — Innovation Capital Law Group, LLP; Vic Lin

(57) ABSTRACT

Disclosed is application of obacunone in the manufacture of a medicament for prevention or treatment of lung injury and pulmonary fibrosis. The medicament consists of obacunone and pharmaceutically acceptable auxiliaries and additives, wherein obacunone is 3% to 25% by mass in the medicament. The obacunone in the medicament can inhibit bleomycin-induced lung injury and pulmonary fibrosis in mice, and regulate the expression of the inflammation-associated cytokines in the bleomycin-induced injured lung tissue in mice.

10 Claims, 5 Drawing Sheets

APPLICATION OF OBACUNONE IN PREPARATION OF DRUG FOR PREVENTING AND TREATING LUNG DAMAGE AND PULMONARY FIBROSIS

TECHNICAL FIELD

The present invention relates to a medical formulation containing organic active ingredients, and particularly to the anti-lung injury and anti-pulmonary fibrosis activities of a compound having a lactone ring.

BACKGROUND

Lung injury is a common disease, and acute lung injury (ALI) severely affects the human health. ALI is an injury to alveolar epithelial cells and capillary endothelial cells caused by various direct and indirect insults, and leads to diffuse pulmonary interstitial edema and alveolar edema, and also to acute hypoxic respiratory insufficiency which is an early stage of acute respiratory distress syndrome (ARDS). Pulmonary fibrosis (PF) is an interstitial lung disease having very poor prognosis and severely affecting the quality of life of patients, and is one of the most serious diseases in the respiratory system. At present, studies have shown that PF results from lung injury, characterized by migration, attachment and proliferation of fibroblasts in the alveolar space. In recent years the mortality of early-stage ALI has been considerably improved, but late-stage PF directly and indirectly results in death of patients. It was found that 55% of lung biopsy from ALI deaths showed severe PF.

*Dictamnusdasycarpus* Turcz is a Traditional Chinese drug. It is isolated from *Dictamnusdasycarpus* root bark and has a strong special smell. *Dictamnusdasycarpus Turcz*. tastes bitter, has a cold nature, follows the spleen, stomach and bladdermeridian, and is effective in dispelling wind pathogen and eliminating dampness pathogen, clearing away heat-toxicity, relieving itching, and disinfecting insects. Obacunone is a limonoid extracted from *Dictamnusdasycarpus Turcz*, having a formula of $C_{26}H_{30}O_7$ and a structure of formula (I) below.

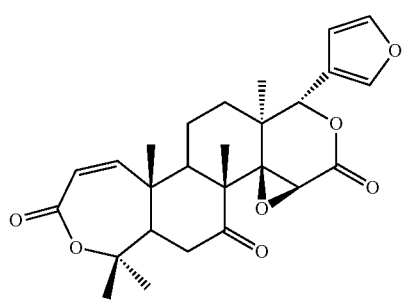

(I)

Research has shown that obacunone exhibits an anti-tumor effect. A study on human colon cancer cells (SW480) showed that obacunone induced cell apoptosis by activating cytochrome C, and suppressed growth of tumor cells by activating p21 to arrest the cell cycle at phases G2/M and G1. A study on human pancreatic cancer cells (Panc-28) demonstrated that obacunone induced apoptosis of tumor cells by activating p53. Furthermore, obacunone also has an effect of inhibiting activity of arginase and reciprocally increasing NO production through enhancing stabilization of the endothelial NO synthase dimer, and thus can produce a certain therapeutic effect on cardiovascular diseases caused by endothelial functional disorder. However, a function of obacunone in prevention or treatment of lung injury and pulmonary fibrosis has not been reported yet.

SUMMARY

A technical problem to be solved by the present invention is to provide a new use of obacunone, i.e. a new application thereof in pharmaceutics.

The new application in pharmaceutics is an application of obacunone in the manufacture of a medicament for prevention or treatment of lung injury and pulmonary fibrosis.

In the above application, the medicament consists of obacunone and pharmaceutically acceptable auxiliaries, wherein obacunone is 3% to 25% by mass in the medicament. The medicament may be an injection, or a common oral formulation, such as a tablet or capsule.

The obacunone according to the present invention may be conventionally extracted from the Traditional Chinese drug *Dictamnusdasycarpus Turcz* or other plants, or prepared by synthesis or other methods.

The application according to the present invention lies in the finding that the compound obacunone having said use can inhibit lung injury and pulmonary fibrosis of mice induced by bleomycin, and regulate expressions of inflammation-related cytokines in the bleomycin-induced injured lung tissue of mice, thereby not only having a significant effect of preventing and treating lung injury and pulmonary fibrosis, but also having the advantages of low toxicity and no damage to liver and kidney.

DETAILED DESCRIPTION

I. Examples of Drug Efficacy

Experiment 1: Inhibition of Bleomycin-Induced Lung Injury and Pulmonary Fibrosis by Obacunone In Vivo 1. Experimental Materials 1.1 Experimental Animals Eighteen C57BL/6 mice, aged 8 weeks, each weighing 18 to 22 g, were provided by the Laboratory Animal Center of Guangzhou University of Chinese Medicine (Certificate No. 44007200023897).

1.2 Drugs, Reagents and Apparatus

Obacunone (purchased from Tianjin Shilan Science and Technique Co. Ltd.); corn oil (Guangdong Changxing Food Trading Co. Ltd.); DMSO (Sigma); PBS (Hyclone Development); HE staining solution (Guge Biological Sciences);

Masson triple-staining kit (Fuzhou Maxim Biotechnologies); anhydrous ethanol (Damao); xylene (Damao); inverted phase contrast microscope (CKX41, Olympus); automated cell counter (Countstar IC-100); biosafety cabinet (BSC-1000IIAC); fully-automated staining-mounting integrated workstation (LEICA ST5020); tissue embedding console (HisTOSTAR); fully-automated closed tissue dehydrator (SHANDON PATACENTRE); semi-automated rotary microtome (LEICA RM2245).

2. Experimental Methods and Results

Bleomycin was intraperitoneally injected into 8-week old B6 mice at a dose of 2 mg/mouse, once per week, three times in total. 48 hours before each injection with bleomycin, corn oil or 10 mg/kg obacunone was intraperitoneally injected into B6 mice in advance. 7 days after the last injection with bleomycin, lung tissue was isolated, fixed, sectioned, HE-stained (see Experiment 8 for details), and Masson-stained.

Figure 1:
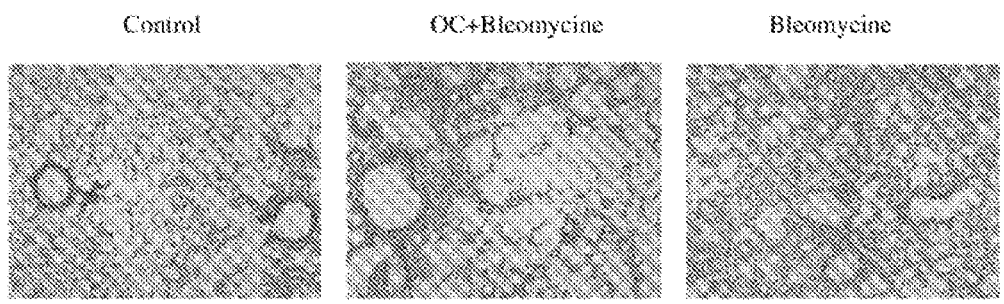
FIG. 1 is a microphotograph showing the pathological result of inhibition of bleomycin-induced lung injury in mice by obacunone.
Figure 1:
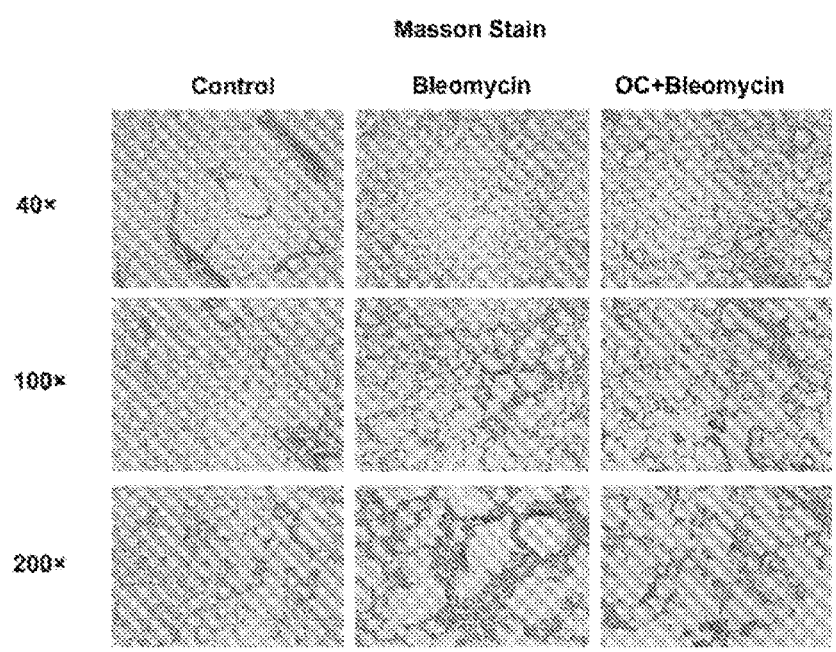
Figure 2A:
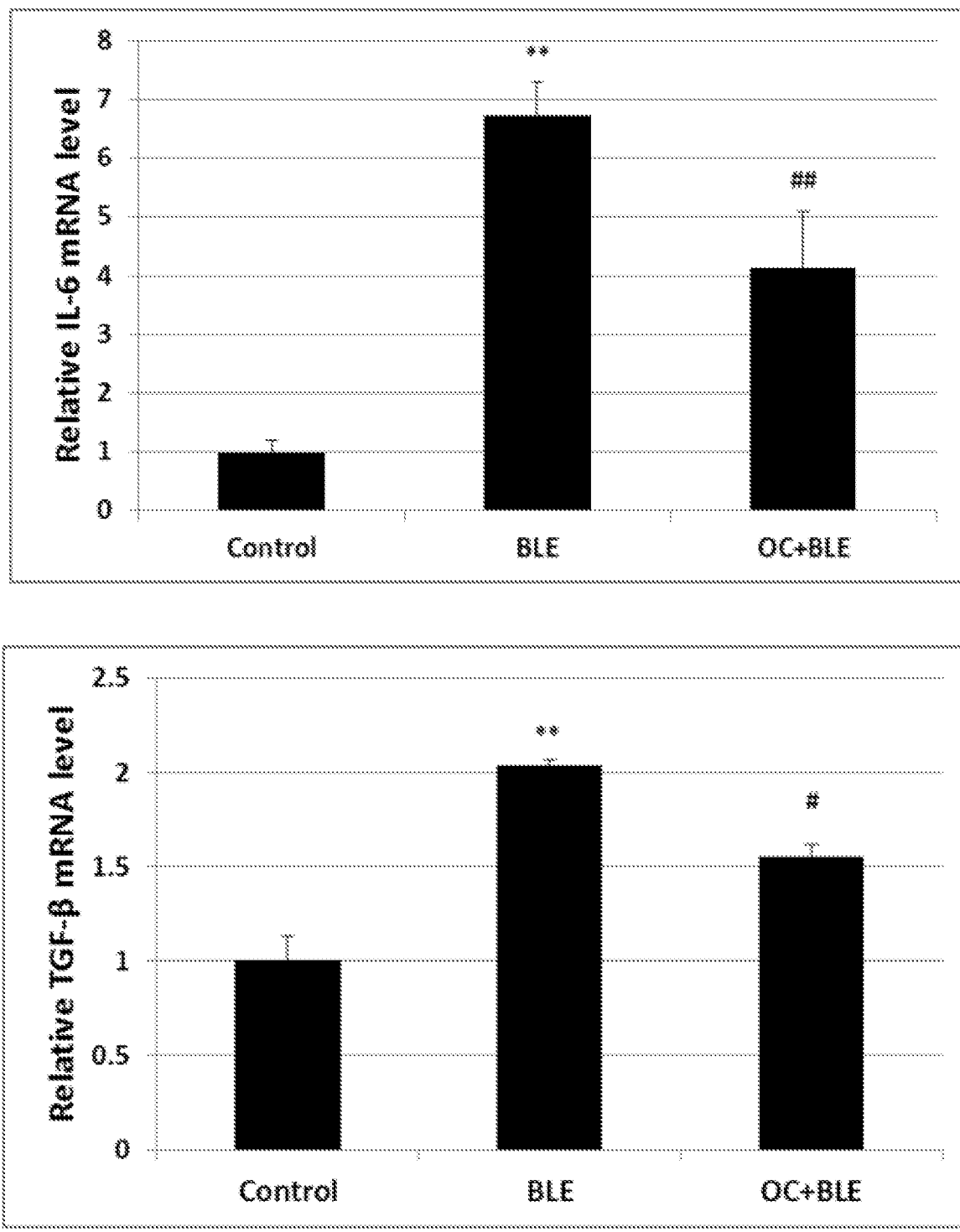
FIG. 2 is a histogram showing the result of regulation, by obacunone, of expressions of inflammation-related cytokines in the bleomycin-induced injured lung tissue of mice.
Figure 2B:
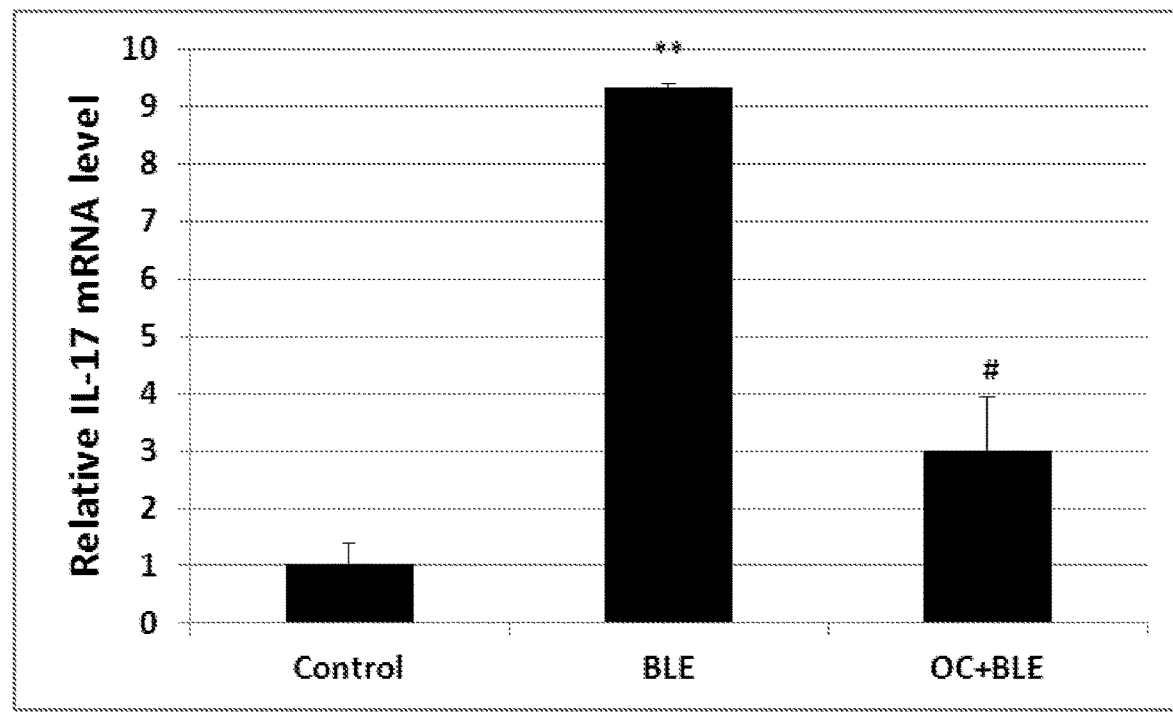
Figure 2B:
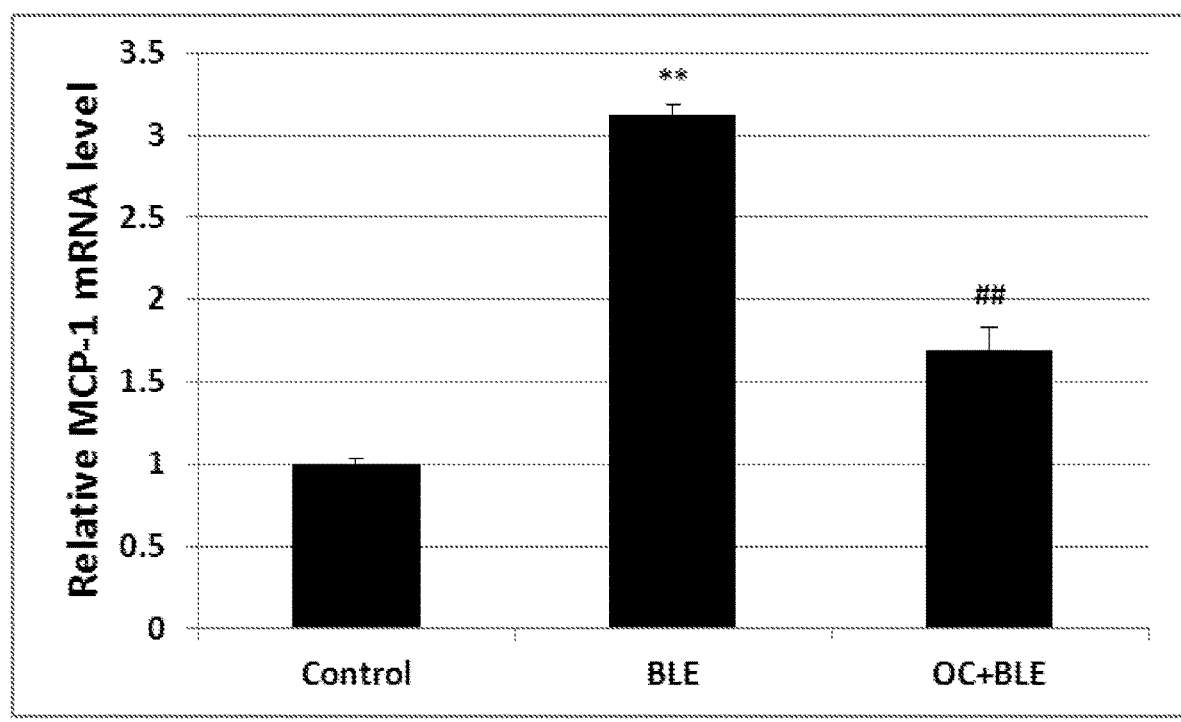
Figure 2C:
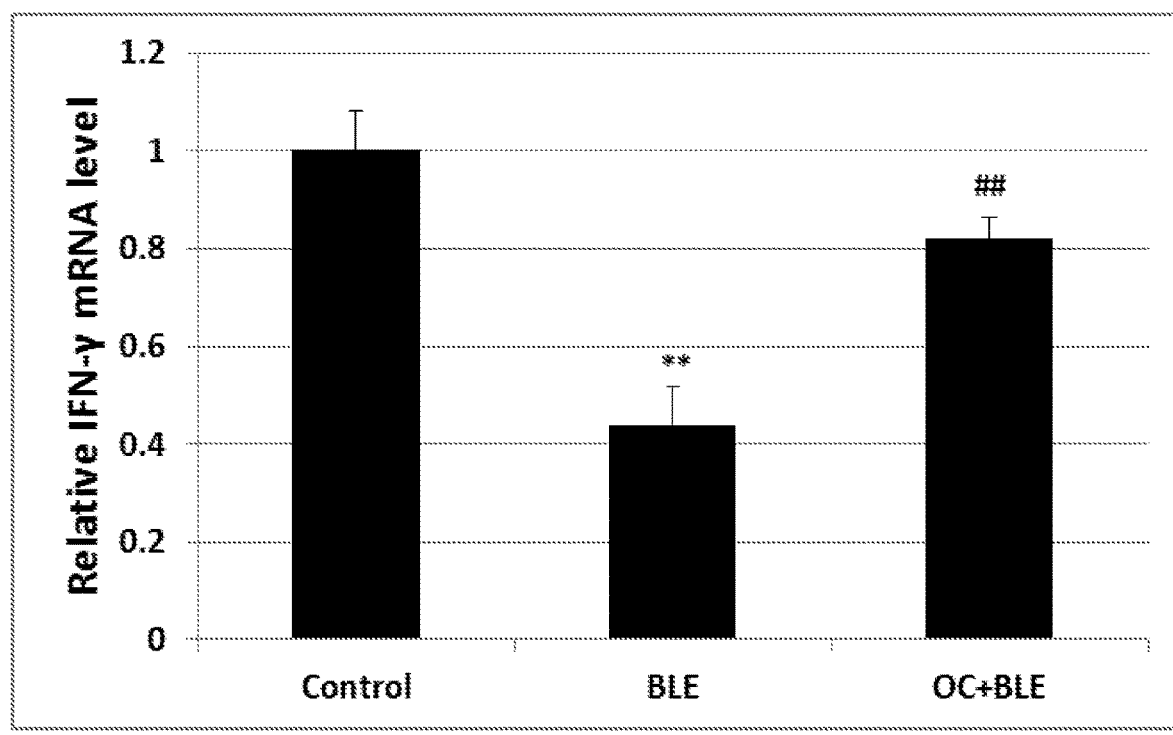

The HE staining showed that, as compared to the sections of normal lung tissue of B6 mice, it was found in the sections of lung tissue in the bleomycin group that a large number of pulmonary alveoli shrank, infiltration of inflammatory cells can be seen in the alveolar space, the walls of some alveoli were thickened or broken, bullae were formed, and a large number of cells of interstitial tissue of lung were proliferated. In contrast, the lung tissue of the mice group pre-injected with obacunone exhibited significant improvement of the above pathological changes (FIG. 1A).

The Masson staining showed that the most area in the field in the bleomycin group was stained with aniline blue, indicating extensive precipitation of stroma, such as collagen and fibronectin. In contrast, the mice group pre-injected intraperitoneally with obacunone exhibited significant improvement of the above pathological changes (FIG. 1B).

Experiment 2: Obacunone Inhibited Bleomycin-Induced Expression of Inflammatory Factors 1. Experimental Materials 1.1 Experimental Animals
Eighteen C57BL/6 mice, aged 8 weeks, each weighing 18 to 22 g, were provided by the Laboratory Animal Center of Guangzhou University of Chinese Medicine (Certificate No. 44007200023897).
1.2 Drugs, Reagents and Apparatus
Obacunone (purchased from Tianjin Shilan Science and Technique Co. Ltd.); corn oil (Guangdong Changxing Food Trading Co. Ltd.); DMSO (Sigma); TRIzol (Life Company); primers (Beijing Genomics Institute); low-speed desktop automatically-balanced centrifuge (DT5-3); CFX96 Touch™ fluorescent quantitative PCR detection system (Bio-Rad).

2. Experimental Methods and Results

The mRNA levels of cytokines IL-6, TGF-β, IL-17, IFN-γ and MCP-1 were analyzed by qPCR. *P<0.05, **P<0.01 indicated significant differences between the BLM injection group and the normal group; # P<0.05, ## P<0.01 indicated significant differences between the BLM injection group and the BLM+obacunone injection group.

Bleomycin significantly induced changes in expression of related cytokines in lung tissue, such as IL-6, TGF-β, IL-17, IFN-γ and MCP-1, among which IL-6, TGF-β, IL-17 and MCP-1 significantly increased, and IFN-γ significantly reduced. These cytokines are associated with inflammation, and TGF-β was also associated with induction of fibrosis in tissue. Obacunone repaired these bleomycin-induced changes to a great extent (FIG. 2).

Experiment 3: Obacunone Inhibited α-SMA Expression of Bleomycin-Induced Pulmonary Fibrosis 1. Experimental Materials 1.1 Experimental Animals
Eighteen C57BL/6 mice, aged 8 weeks, each weighing 18 to 22 g, were provided by the Laboratory Animal Center of Guangzhou University of Chinese Medicine (Certificate No. 44007200023897).
1.2 Drugs, Reagents and Apparatus
Obacunone (purchased from Tianjin Shilan Science and Technique Co. Ltd.); corn oil (Guangdong Changxing Food Trading Co. Ltd.); DMSO (Sigma); anhydrous ethanol (Damao); xylene (Damao); DAB color development kit (Fuzhou Maxim); immunohistochemistry staining kit (Fuzhou Maxim); inverted phase contrast microscope (CKX41, Olympus); biosafety cabinet (BSC-1000IIAC); fully automated staining-mounting integrated workstation (LEICA ST5020); tissue embedding console (HisTOSTAR); fully-automated closed tissue dehydrator (SHANDON PATACENTRE); semi-automated rotary microtome (LEICA RM2245).

2. Experimental Methods and Results

In pulmonary fibrosis TGF-β induced lung interstitial fibroblasts to transform into myofibroblasts, of which the marker is the expression of α-smooth muscle actin (α-SMA). Therefore, in this experiment the effect of obacunone on the expression of α-SMA in lung myofibroblasts was investigated to provide experimental support for the use of obacunone in treatment and prevention of pulmonary fibrosis.

Steps of immunohistochemistry staining are as follows:
1) placing and baking paraffin wax sections in an electrothermal thermostat oven at 60° C. for 30 min;
2) dewaxing the sections with xylene (8 min for each of I and II), hydrating them with decreasing concentrations of ethanol (8 min for each concentration), and washing with water;
3) performing antigen retrieval, and washing the sections with PBS (3 times×3 min);
4) adding Solution A (S-P kit) dropwise, blocking at room temperature for 10 min, and washing the sections with PBS (3 times×3 min);
5) adding Solution B (S-P kit) dropwise, blocking at room temperature for 10 min, and blotting extra liquid;
6) adding a primary antibody dropwise, placing the sections in a wet box overnight at 4° C., and washing the sections with PBS (3 times×3 min);
7) adding Solution C (S-P kit) dropwise, leaving at room temperature for 10 min, and washing the sections with PBS (3 times×3 min);
8) adding Solution D (S-P kit) dropwise, leaving at room temperature for 10 min, and washing the sections with PBS (3 times×3 min);
9) DAB-coloring the sections, and washing the sections with water;

10) counterstaining the sections with hematoxylin for 1 min at room temperature; washing the sections with water; allowing differentiation with 0.5% HCl ethanol, re-bluing with PBS, and washing with water;

11) dehydrating with increasing concentrations of ethanol, clarifying with xylene, and mounting.

Figure 3:
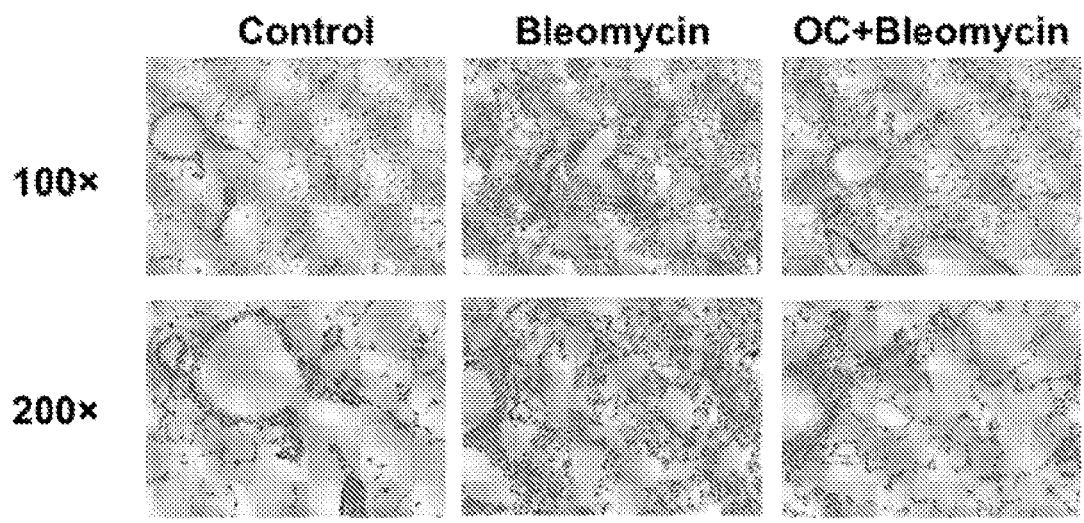
FIG. 3 is a microphotograph showing the inhibition result of obacunone to bleomycin-induced pulmonary fibrosis (expression of α-SMA).

The results showed that the expression of α-SMA in lung tissue of mice with bleomycin was significantly higher than that in the normal group, and mainly seen in alveolar epithelial cells, bronchiolar epithelial cells, macrophages, and vascular endothelial cells. However, after administration of obacunone, the expression of α-SMA was significantly reduced as compared to the bleomycin group (FIG. 3), indicating that obacunone significantly inhibited the course of bleomycin-induced pulmonary fibrosis.

Experiment 4: Experiment on Damage Caused by Obacunone to Liver and Kidney of Mice 1. Experimental Materials 1.1 Experimental Animals Eighteen C57BL/6 mice, aged 8 weeks, each weighing 18 to 22 g, were provided by the Laboratory Animal Center of Guangzhou University of Chinese Medicine (Certificate No. 44007200023897).

1.2 Drugs, Reagents and Apparatus

Obacunone (purchased from Tianjin Shilan Science and Technique Co. Ltd.); corn oil (Guangdong Changxing Food Trading Co. Ltd.); DMSO (Sigma); PBS (Hyclone Development); HE staining solution (Guge Biological Sciences); anhydrous ethanol (Damao); xylene (Damao); inverted phase contrast microscope (CKX41, Olympus); fully-automated cell counter (Countstar IC-100); biosafety cabinet (BSC-1000IIAC); fully-automated staining-mounting integrated workstation (LEICA ST5020); tissue embedding console (HisTOSTAR); fully automated closed tissue dehydrator (SHANDON PATACENTRE); semi-automated rotary microtome (LEICA RM2245).

2. Experimental Methods and Results 8-week aged B6 mice were injected with corn oil or 10 mg/kg obacunone, twice a week, 6 times in total. 7 days after the last injection, liver and kidney tissues were isolated, fixed, sectioned, and HE-stained (FIG. 4), as described below.

HE (Hematoxylin-eosin) staining: the paraffin wax samples were continuously sectioned with the semi-automated rotary microtome, with a thickness of 3.5 μm; for staining, the sections were baked and dried for 20 min, rinsed with xylene (2 times×10 min), with anhydrous ethanol (2 times×2 min), with 95% ethanol for 1 min, with 80% ethanol for 1 min, with 70% ethanol for 1 min, washed with water for 1 min, then stained with hematoxylin for 8 min, with hematoxylin for 10 min, washed with water (2 times×1 min), with 0.5% HCl-ethanol for 10 sec, washed with water for 10 min, stained with eosin for 2 min, washed with water for 1 min, with 80% ethanol for 5 sec, with 85% ethanol for 5 sec, with 90% ethanol for 5 sec, with 95% ethanol for 1 min, with anhydrous ethanol (2 times×2 min), with anhydrous ethanol for 3 min, and with xylene (2 times×2 min), and then the staining was completed and the sections were directly mounted with neutral gum.

Figure 4:
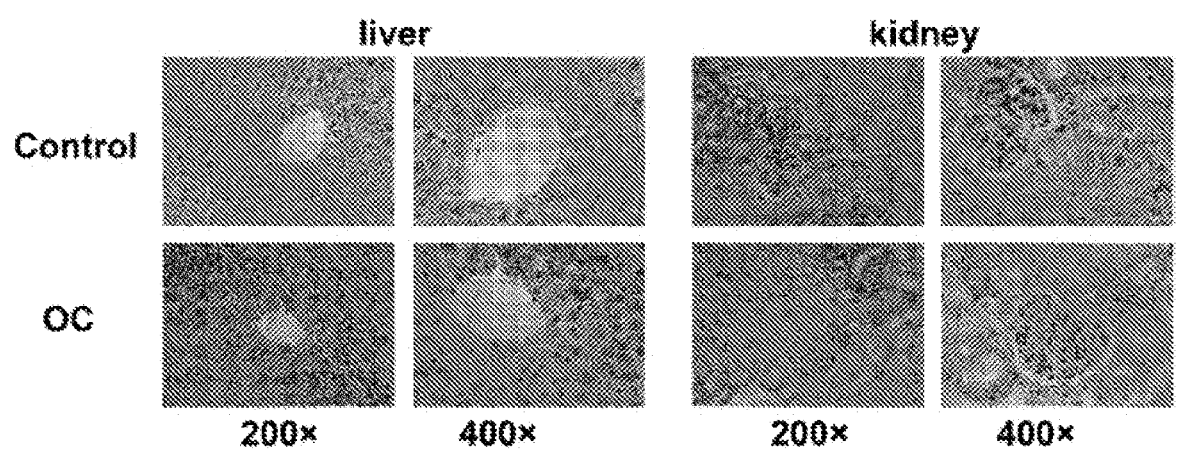
FIG. 4 is a microphotograph showing that obacunone causes no damage to the livers and kidneys of mice.

As shown in FIG. 4, obacunone did not apparently affect the liver and kidney of mice. In the sections of liver, intact structures of hepatic sinusoid and hepatic cord can be seen, and no nuclear edema or cytoplasmic pathological changes can be seen in the liver. In the sections of kidney, it can be seen that kidney glomeruli have intact structures and are in a number consistent with that in the control group, and no pathological changes can be seen in the cytoplasm or nuclei.

In summary, the above studies demonstrate that: obacunone significantly inhibits pulmonary inflammation and fibrosis process without considerable toxic and side effects, and therefore exhibits an excellent effect against lung injury and pulmonary fibrosis.

II. Examples of Preparation of Pharmaceutical Formulations

Example 1: Injection

1. Formula

| | |
|---|---|
| Obacunone | 30 g |
| Corn oil (injection grade) | 270 g |
| PEG15-hydroxystearate | 18 g |
| Soybean phospholipid (injection grade) | 2 g |
| Glycerol (injection grade) | 2 g |
| Oleic acid | 5 g |
| Sodium phytate | 0.5 g |
| Injection water | To 1000 ml |

2. Preparation Method

Obacunone was immersed in soybean oil and oleic acid to form an oil phase, and heated to 70° C. under continuous stirring. PEG15-hydroxystearate, soybean phospholipid, glycerol, and sodium phytate were dispersed in water to form an aqueous phase, and heated to 70° C. under continuous stirring. The oil phase was added slowly to the aqueous phase, and the mixture was stirred at a high speed for 8 min (at 2000 rpm) in a high-speed disperser to obtain a crude emulsion. The crude emulsion was homogenized for 7 times through a high-pressure homogenizer (at a pressure of 65 MPa and 75° C.), diluted to 1000 ml with injection water, pre-filtered through a 0.45 μm microporous filter, aliquoted and sealed under $N_2$, and autoclaved (121° C. for 15 min), to obtain the formulation. Each aliquot contained 1 ml. The formulation was administered by intramuscular injection once a day, two aliquots per injection. The administration may last 2 to 3 courses of treatment, with 10 to 20 days per course.

Example 2: Tablet

1. Formula

| | |
|---|---|
| Obacunone | 300 g |
| Hydroxypropylcellulose SSL | 80 g |
| Liquid paraffin wax | 1000 ml |
| Cross-linked carboxymethylcellulose sodium | 20 g |
| Magnesium stearate | 2 g |

2. Preparation Method

Obacunone and hydroxypropylcellulose SSL were dissolved in 800 ml ethanol, and the solution was added to liquid paraffin wax. Ethanol was removed by drying under reduced pressure, and the obacunone and hydroxypropylcellulose formed microparticles and were precipitated. The precipitated microparticles were dried at 50° C., and thoroughly mixed with 100-mesh-screened cross-linked carboxymethylcellulose sodium and magnesium stearate. The mixture was compressed into 10,000 tablets. Each tablet contained 30 mg obacunone and was 0.13 g (net weight).

Two tablets were orally administered once per day. The administration may last 2 to 3 courses of treatment, with 10 to 20 days per course.

Example 3: Capsule

1. Formula

| | |
|---|---|
| Obacunone | 20 g |
| Low-substituted hydroxypropylcellulose | 50 g |
| Cross-linked povidone | 5 g |
| Sodium dodecylsulfate (SDS) | 2 g |
| Povidone K30 | 5 g |
| Magnesium stearate | 3 g |

2. Preparation Method

SDS and povidone K30 in the formula amounts were weighed out and dissolved in water to prepare a 10% solution of povidone K30 as a binder. Obacunone in the formula amount was weighed out as a crude drug and placed in a mixer, to which the binder was then added to prepare a soft material. The soft material was further granulated in a granulator. The wet granules were dried at 40° C. to 45° C. for 1 to 3 hours, and rounded. The resultant granules were placed in a mixer and mixed with 60-mesh-screened low-substituted hydroxypropylcellulose, cross-linked povidone, and magnesium stearate for 30 min. Samples were taken for measurement of contents and weight loss upon drying. According to the measurement result of the granule content, the average loading amount was calculated and filling was performed with a 4# capsule. 1,000 capsules were made. Each capsule was filled with 0.1 g granules and contained 20 mg obacunone. Three capsules were orally administered once per day. The administration may be continuous, with 10 to 20 days per course of treatment.

The invention claimed is:

1. A method for treatment of lung injury and pulmonary fibrosis comprising administering a medicament having obacunone to a patient in need thereof.

2. The method according to claim 1, wherein the medicament includes obacunone and pharmaceutically acceptable auxiliaries and additives, wherein obacunone is 3% to 25% by mass in the medicament.

3. The method according to claim 1, wherein the medicament is an injection, a tablet, or a capsule.

4. The method according to claim 3, wherein the injection includes the following raw materials per 1000 ml:

| | |
|---|---|
| Obacunone | 30 g, |
| injection-grade corn oil | 270 g, |
| PEG15-hydroxystearate | 18 g, |
| injection-grade soybean phospholipid | 2 g, |
| injection-grade glycerol | 2 g, |
| oleic acid | 5 g, |
| sodium phytate | 0.5 g, and |
| the balance of water. | |

5. The method according to claim 3, wherein the tablets include the following raw materials per 10000 tablets:

| | |
|---|---|
| obacunone | 300 g, |
| hydroxypropylcellulose SSL | 80 g, |
| liquid paraffin wax | 1000 ml, |
| cross-linked carboxymethylcellulose sodium | 20 g, and |
| magnesium stearate | 2 g. |

6. The method according to claim 3, wherein the capsules include the following raw materials per 1000 capsules:

| | |
|---|---|
| Obacunone | 20 g, |
| low-substituted hydroxypropylcellulose | 50 g, |
| cross-linked povidone | 5 g, |
| sodium dodecylsulfate | 2 g, |
| povidone K30 | 5 g, and |
| magnesium stearate | 3 g. |

7. The method according to claim 2, wherein the medicament is an injection, a tablet, or a capsule.

8. The method according to claim 7, wherein the injection includes the following raw materials per 1000 ml:

| | |
|---|---|
| Obacunone | 30 g, |
| injection-grade corn oil | 270 g, |
| PEG15-hydroxystearate | 18 g, |
| injection-grade soybean phospholipid | 2 g, |
| injection-grade glycerol | 2 g, |
| oleic acid | 5 g, |
| sodium phytate | 0.5 g, and |
| the balance of water. | |

9. The method according to claim 7, wherein the tablets include the following raw materials per 10000 tablets:

| | |
|---|---|
| obacunone | 300 g, |
| hydroxypropylcellulose SSL | 80 g, |
| liquid paraffin wax | 1000 ml, |
| cross-linked carboxymethylcellulose sodium | 20 g, and |
| magnesium stearate | 2 g. |

10. The method according to claim 7, wherein the capsules include the following raw materials per 1000 capsules:

| | |
|---|---|
| Obacunone | 20 g, |
| low-substituted hydroxypropylcellulose | 50 g, |
| cross-linked povidone | 5 g, |
| sodium dodecylsulfate | 2 g, |
| povidone K30 | 5 g, and |
| magnesium stearate | 3 g. |

* * * * *